United States Patent [19]

Nemec et al.

[11] Patent Number: 5,575,998
[45] Date of Patent: Nov. 19, 1996

[54] MIXTURE OF MICROORGANISMS, ITS USE FOR THE BIODEGRADATION OF HYDROCARBONS, AS WELL AS PROCESS FOR ITS APPLICATION

[75] Inventors: Miroslav Nemec, Ceska; Dana Horakova, Brno, both of Czech Rep.

[73] Assignee: Biorem AG, Zug, Switzerland

[21] Appl. No.: 318,825

[22] PCT Filed: Apr. 13, 1993

[86] PCT No.: PCT/EP93/00897

§ 371 Date: Nov. 21, 1994

§ 102(e) Date: Nov. 21, 1994

[87] PCT Pub. No.: WO93/21348

PCT Pub. Date: Oct. 28, 1993

[30] Foreign Application Priority Data

Apr. 15, 1992 [CZ] Czech Rep. .............................. 1157-92

[51] Int. Cl.$^6$ .......................... C02F 3/00; A01N 63/00; C12N 1/00
[52] U.S. Cl. .......................... 424/93.3; 210/601; 210/610; 210/611; 424/93.47; 424/93.5; 424/93.51; 435/252.1; 435/262.5; 435/877; 435/911
[58] Field of Search .................................. 210/601, 610, 210/611; 424/93.3, 93.47, 93.5, 93.51; 435/252.1, 262.5, 877, 911

[56] References Cited

U.S. PATENT DOCUMENTS

| 4,415,661 | 11/1983 | Thirumalachar et al. | 435/174 |
| 4,535,061 | 8/1985 | Chakrabarty et al. | 435/253 |
| 4,593,003 | 6/1986 | Vandenbergh | 435/172.3 |

FOREIGN PATENT DOCUMENTS

| 0270805 | 6/1988 | European Pat. Off. . |
| 0289350 | 11/1988 | European Pat. Off. . |

OTHER PUBLICATIONS

Kyokaishi, "Id. of three phenol degrading microorg. from nature and their char." Abstr., 1987.

*Primary Examiner*—John W. Rollins
*Assistant Examiner*—Deborah K. Ware
*Attorney, Agent, or Firm*—Edwin D. Schindler

[57] ABSTRACT

The mixture of natural microorganisms causes a biodegradation of mineral oils and mineral oil products. It contains *Pseudomonas putida* and *Geotrichum candidum* in a ratio of the cell-numbers of 5:1 to 1:1. The mixture is induced by a cultivation in the presence of oil-acid. Afterwards, one works with it on hydrocarbons under the supply of oxygen as well as in the presence of stimulation-substances at a pH-value of 4.5 to 7.5 and at a temperature of 5°+C. to 35° C.

16 Claims, No Drawings

MIXTURE OF MICROORGANISMS, ITS USE FOR THE BIODEGRADATION OF HYDROCARBONS, AS WELL AS PROCESS FOR ITS APPLICATION

BACKGROUND OF THE INVENTION

1. Technical Field of the Invention

The invention relates to a mixture of natural microorganisms, which, in its special composition, is capable of biologically degrading hydrocarbons. The invention is especially useful in degrading mineral oil, mineral oil by-products and related hydrocarbons. Further, the invention relates to the use of this mixture for the biodegradation of hydrocarbons. The invention teaches a special process for the cultivation and application of the mixture for the biodegradation of oil-contaminated soils and waters.

2. Description of the Prior Art

The interest in the focussed use of microorganisms for the biological degradation of mineral oil, its derivates and products has increased in the recent years. As early as in 1903, the first organisms have been described which use hydrocarbons as a source for carbons and energy. At present, more than 40 species of microorganisms are known which use aliphatic or aromatic hydrocarbons in the course of a biological degradation. These organisms have been isolated from the oceans, from sweet-waters as well as from the soil.

The number of bacteria and mushrooms which are able to biologically degrade mineral-oil hydrocarbons, increases sharply and locally after oil spills. These substances occur in a substantial part as selection-gas.

From a genetic view point it is clear that the ability of a major proportion of microorganisms to degrade mineral-oil hydrocarbons is controlled by plasmid. By the proof of the transfer of plasmid it became possible to explain the sharp increase of the number of organisms with degrading ability.

As a subtrate for microorganisms, mineral oil is an extremely complex mixture of hydrocarbons. The saturated fraction of mineral oil includes n-alkanes, branching alkanes and cyclo-alkanes. The biodegradation of the n-alkanes up to $C_{44}$ is in most cases realized by the monoterminal attack under the creation of carbonacids. This process may lead to an accumulation of some more or less toxic fat-acids.

The branching isoprenoid alkanes are degraded by w-oxidation under the creation of dicarbon-acids. The terminal branched alkanes are very resistant to a biodegradation. They block the β-oxidation and have the tendency to accumulate within the milieu. After the spontaneous degradation of a hydrocarbon-contamination, tripentacyclic bindings are often created, which are persistent in the milieu. Because of that it is clear that the qualitative composition of the oil and its products have a high influence on their degradability.

In the metabolism of the mineral-oil hydrocarbons two other processes play an important role—the cooxidation and prolongation. Many oil-components which are not degradable according to the opinion of many skilled professionals, are degradable when they occur in presence of other hydrocarbons which allow the growth of the microorganisms. The degradation process of microorganisms by the inventive mixture is in no way comparable with the ability of the pure species to degrade the single hydrocarbons.

The speed of the microbial degradation of the mineral-oil hydrocarbons is influenced by many factors which directly or indirectly have an influence on the growth and the metabolism of the microbial population. As crucial appears the physical condition of the hydrocarbons, since the hydrocarbons are degraded the most intensively on the "separation-line" between water and hydrocarbon. Further abiotic factors are the temperature and the nutrions which are available. Most heterotroph microorganisms are able to degrade hydrocarbons within a wide temperature range of 0° C. to 70° C. The temperature not only has an influence on the speed of the degradation but above all on the physical condition of the hydrocarbons, which is in a close connection to the selective pressure of the temperature on microbial communities which are created by the eco-system. In the course of the complex evaluation, the temperature must be considered in connection with other factors. In any case, the temperature must not necessarily be a limiting factor.

The speed of the degradation of mineral oil-products is substantially influenced by the presence of nitrogen and phosphor, which are commonly incorporated in the biomass with hydrocarbon-containing splitting substances. The optimal mass-ratios between hydrocarbon and nitrogen on the one side and between hydrocarbon and phosphor on the other side depend on the qualitative composition of the mineral oil or the mineral oil-products and of the abiotic factors of the milieu. Nitrogen and phosphor are also the common components of "stimulators" which stimulate the biodegradation processes.

For the industrial application of microorganisms in the course of the reclamation of contaminated soils or waters, the degradation rate and the quality of the degradation are of highest interest. For the acceleration of the degradation rate, the following distinct main-categories are known:

1. Fertilization: This method is restricted to only the optimalization of the milieu for the microorganisms which are inherent in the contaminated soil or water. One takes it as a basis that in such a contaminated soil or water, oil-degrading microorganisms in sufficient quality and quantity are present anyway, and concentrates the activities to the addition of nitrogen, phosphor, calcium as well as some trace elements, and to the support of the breathing ability of the present, always aerobic microorganisms by supplying air. For this purpose, the soil is loosened and turned on a regular basis, or air is being pumped into the soil by means of air-lines and pumps. In many cases, a heap of several meters height is equipped with a number of perforated tubes going through the heap on several levels whereby the tubes are being put under air-pressure or vacuum (vacuum-heap-system). The professionals favor this system and are confident that it will be most successful since one thinks that after an oil spill, oil-degrading microorganisms will quickly be present in sufficient quantity, and the degradation is only restricted by the lack of nutrition- and air-supply for the organisms.

2. Seeding: As a separate technique or additional to the above mentioned method, the seeding-technique is used. Seeding means the application of additional oil-degrading microorganisms into the contaminated material. Such preparations which are used by different companies on sites with oil-contaminations usually contain only a single species. The application of such preparations is adequate for fresh contaminations where eventual products of the metabolism are present which appear because of the natural present organisms. The opinion is established among the professionals that the additional application of more natural microorganisms does not substantially increase the effectiveness of the degradation. Moreover, the public in general has some reservations against the transplantation of foreign microorganisms since—be it reasonable or not—one is afraid of there uncontrolled growth, accompanied by unnecessary side effects, which may even be toxic.

3. GEM: This is an abbrevation for "Genetically Engineered Microorganisms", which have very effective qualities in view of their oil-degradation capability. The reservations against the use of such GEM's are the strongest. Therefore, their application will most likely be more and more restricted.

SUMMARY OF THE INVENTION

The objective of the present invention is to create a mixture of natural microorganisms which has a higher degradation rate for hydrocarbons in soils and waters and which is easy to cultivate and to apply in practice. Moreover it is an objective of this invention to teach how this mixture is used and as well as to teach a process for its cultivation and application.

This objective is solved by a mixture of natural microorganisms for the biodegradation of hydrocarbons, in particular for mineral oil and mineral oil-products, consisting of *PSEUDOMONAS PUTIDA* and *GEOTRICHUM CANDIDUM* in a ratio of the cell-number of between 5:1 to 1:1.

For its use in the course of the reclamation of contaminated soils and waters, it is applied at a pH-value of between 4.5 and 7.5 and in a temperature-range of 5° C. to 35° C. in a quantity of between 1 and 10 grams per liter of applicable preparation. For each square meter of contaminated soil, some 5 to 20 liters of applicable preparation is used, one or several times.

The process for its use includes basically the one-time or several-time spraying of the mixture solved in water unto the contaminated mass and afterwards the optimalization of the milieu in the contaminated mass by the supply of air and nutrions according to the known methods.

The invention starts with the knowledge that it is possible, in contradistiction to the widely spread opinion of professionals, that the degradation speed of oil-substances, as they are given by the locally natural occuring microorganism-communities in an already optimized milieu, may be considerably increased by the addition of artificially cultivated communities of natural microorganisms, which have a higher affinity to the present substances.

Very advantageous is the application of artificially composed and cultivated communities of natural microorganisms which have the capability to use the coordination processes in a greater extent and thereby to accelerate the degradation processes considerably and creating a "quality improvement" on them.

The inventive mixture allows a more effective use of the substrate of the mineral oil-substances by a unification or by a mixture (consortium) of natural microorganisms. The gist of the invention is a mixture of microorganisms which contains the microorganisms *PSEUDOMONAS PUTIDA* and *GEOTRICHUM CANDIDUM* in a ratio of their cell numbers of 5:1 to 1:1. Both organisms have been isolated in the vicinity of an oil well in Hodonin in the Czech Republic. After their isolation, the microorganisms have not been prepared genetically, but remained in their natural condition.

DETAILED DESCRIPTION OF THE INVENTION

*PSEUDOMONAS PUTIDA* is a common contaminant of the soil, the water and the plants. It may also be found in the vicinity of hospitals. Rarely it is isolated from clinical samples as opportun pathogen.

*GEOTRICHUM CANDIDUM* on the other side is a common contaminant of milk as well as of contaminated water. In rare cases it is present in clinic material as conditionally pathogen for both humans and animals.

Also the mixture itself is neither toxic nor pathologic. This has been proved by extensive scientific tests and it is certified.

Among other tests, the mixture, in the following named BIOREM RC1, has been partly injected intraveneriously in liquid form and partly used as food on 24 rabbits, 60 maizes and 30 guinea-pigs in 6 groups each. The following has been scientifically proved:

1. No loss of weight nor acute or chronical diseases of any type whatsoever have been observed on the treated animals.
2. There was no change in the behavior of the animals observed as e.g. loss of appetite, irritation or apathy.
3. In each group, macroscopic changes on certain organs have been searched, that is on the kidneys, the liver, the lungs, the lymph-lumps and the head. No pathologic or toxicologic changes have been found.

The way of the biodegradation of hydrocarbons with the use of this mixture of microorganisms of *PSEUDOMONAS PUTIDA* and *GEOTRICHUM CANDIDUM* starts with the external multiplication and its induction on a synthetic medium in the presence of oil-acid. After that, one works with the mixture on the hydrocarbons to degrade under the supply of oxygen, in presence of stimulating substances such as nitrogen and phosphor, in some cases with trace elements, whereby the ratio of the carbon and the nitrogen in the course of the effect of the mixture of the abovementioned species is kept in a range of their weight-ratios of 10 to 100:1.

The optimal milieu for a biodegradation of hydrocarbons by this consortium of microorganisms is according to the invention a milieu with a pH-value of 4.5 to 7.5 and a temperature of 5° C. to 35° C.

For the preparation and indication of the mixture of microorganisms according to this invention, it is advisable to use a synthetic material which only contains phosphor and nitrogen in soluble form, as well as oil-acid. It is advantageous to select the starting pH-value of the cultivation medium in the range of 4.5 to 7.5. Under intense airing and at a temperature of 20° C. to 25° C., the cultivation time lasts 4 to 10 days, depending on the requirements of the density of the bacterial suspension. The preparation may then be lyophiliseized or dryed or it may be stored in gel-form by a withdrawal of water.

The preparation may be used by the "ex situ"-method or by the "in situ"-method, in both cases by spraying onto the contaminated soil or by inoculation into a contaminated water well, if needed, into water contaminated with mineral oil-substances under contemporaneous addition of a metabolic stimulator. The method also allows the use of a fermentor which is filled with a synthetic milieu, a stimulator and contaminated water. The microbial mixture is added in a quantity in which the optical density is 620 nm (OD620) in the range of 0.60 to 1.90. The pH-value of the milieu is kept within the limits of between 4.5 and 7.5. The degradation process is on-going under aerobic conditions.

In as far as the microbial mixture is applied by spraying onto the ground or soil according to the "ex situ" method, 1 to 10 liters of the mixed culture with an optical density of 620 nm in the range of 0.60 to 1.00 per 1 m$^3$ of soil is used, depending on the moisture and the soil-structure.

For the application by the "in situ" method, 5 to 15 liters of the culture is used per m². In both cases it is necessary to loosen the soil before and after the application, thereby ensuring a sufficient aeration. For the application, the mixed culture contains stimulation substances at the same time.

The result of the application of the inventive mixture of natural microorganisms is a degradation of the major part of the mineral oil-substances present in the environment, which will be degraded into carbon dioxide ($CO_2$) on the one hand, and mounted into the cell material on the other hand. In some cases, the metabolites may be secreted into the surrounding milieu.

The advantages of the mixture and its uses are to be seen in the fact that the created metabolites are not toxic. Furthermore, the high degradation speed in the beginning of the application of the mixture is of great importance. A further advantage is that the number of microorganisms in the course of the application of the preparation is considerably increased in the milieu. This improves the structure of the soil and its replacement into its near original condition. In view of the fact that the organisms used are isolated from the natural environment and that they are not genetically engineered, there is no danger for a negative influence on the biosphere whatsoever.

EXAMPLES FOR THE APPLICATION

Example 1

1,000 ml of the synthetic medium with the initial ratio of carbon:nitrogen:phosphor=800 to 400:6:1 has been inoculated with the prepared and induced cultur (BIOREM RC1), whose optical density was $OD_{620}$=0.650. The cell-number ratio of *Pseudomonas putida:Geotrichum candidum*=3:1. The initial pH-value was 6.0. The cultivation was carried out at temperatures of 20° C. to 25° C. under aeration. The stimulation substance has been added at the beginning of the cultivation and, thereafter, every 5 to 10 days in such a quantity that the ratio between carbon and nitrogen was 60 to 100:1. The quantity of oil-substances has been measured by infrared-spectroscopy, comparing the transmittance of the sample and of the standard at a wavelength of 2920 $cm^{-1}$.

| Sample | RC1 | Quantity of oil-substances in grams per liter (g $l^{-1}$) | | | | |
|---|---|---|---|---|---|---|
| | | Stimulator | 0 days | 10 days | 24 days | 38 days |
| crude oil | + | − | 18.3 | 18.3 | 18.4 | 18.2 |
| crude oil | + | − | 34.1 | 22.1 | 15.0 | 6.1 |
| crude oil | + | + | 34.0 | 18.2 | 11.7 | 1.2 |
| used motor oil | + | + | 18.0 | 7.8 | 1.6 | 0.23 |
| used motor oil and crude oil in ratio of 1:1 | + | + | 18.3 | 8.2 | 3.0 | 0.62 |

Example 2

1,000 ml of the synthetic medium have been inoculated with the prepared induced cultur (BIOREM RC1) in such way, that the optical density was $OD_{620}$=0.700, and at a cell-number ratio of *Pseudomonas putida:Geotrichum candidum*=3:1. The tested mineral oil-products have been added to the mixture until a concentration of 10 g.$l^{-1}$ has been reached. The cultivation was carried out at temperatures of 20° C. to 25° C. under aeration. The stimulation substance has been added regularly after 7 days, under the same conditions as described in example 1. The quantity of oil-substances has been measured by infrared-spectroscopy. The transmittance of the sample and of the standard has been measured at a wavelength of 2920 $cm^{-1}$.

| Sample | Quantity of oil-substances in grams per liter (g $l^{-1}$) | | | |
|---|---|---|---|---|
| | Degradation period | | | |
| | 10 days | 24 days | 38 days | 42 days |
| petroleum RT | 3.58 | 0.34 | 0.21 | 0.21 |
| motor oil | 6.63 | 2.09 | 0.35 | 0.21 |
| MS 8P OLEMS-2 | 4.25 | 1.54 | 0.52 | 0.20 |
| hydraulic liquid AMG 10 | 2.21 | 0.80 | 0.24 | 0.20 |
| gasoline B3V | 3.63 | 2.07 | 0.80 | 0.26 |
| petroleum PN-3 | 2.94 | 1.80 | 0.25 | 0.22 |
| petrol PN-3 with antioxidans: | 2.86 | 1.92 | 0.32 | 0.25 |

Example 3

1,000 ml of the mixed induced culture BIOREM RC1 at the optical density $OD_{620}$=0.600 and at a cell-number ratio of *Pseudomonas putida:Geotrichum candidum*=1:1 has been applied on 1'000 grams of soil which has been contaminated by mineral oil-products due to an oil-spill. The cultivation was carried out in glass-vessels at temperatures of 20° C. to 25° C. Each second day, the soil had been aired by multiple turning. The stimulation substance had been added regularly after 8 to 10 days, under the same conditions as described in example 1. The quantity of mineral oil-substances has been measured by infrared-spectroscopy at a wavelength of 2920 $cm^{-1}$ after extraction of tetrachlor.

| Sample | Quantity of oil-substances in grams per liter (g $l^{-1}$) | | |
|---|---|---|---|
| | Degradation period | | |
| | 10 days | 24 days | 40 days |
| original sample | 1.2 | 1.2 | 1.2 |
| soil + RC1 | 0.61 | 0.57 | 0.09 |
| soil + compost + RC1 | 0.41 | 0.32 | 0.08 |

The contamination of the soil was relatively low and therefore the mixed culture BIOREM RC1 has only been applied at the beginning of the biodegradation process. In case of a higher contaminations the process may be accelerated by repeating the application of the mixed culture in the course of the biodegradation.

Example 4

A quantity of 1,000 ml of synthetic medium had been contaminated with oil in a concentration of 10,000 mg per liter. In the course of the degradation, the ratio between the added nitrogen and the still present carbon has been kept between certain limits. This trial has been made with different oil-derivates and the following degradation rates have been achieved:

| Trial sample Mass of oil-derivates in milligrams per liter (mg l⁻¹) | | | | |
|---|---|---|---|---|
| | Degradation period | | | |
| | 10 days | 20 days | 30 days | 40 days |
| crude oil | 4,920 | 2,420 | 1,080 | 107 |
| motor oil | 4,620 | 1,870 | 280 | 115 |
| old motor oil | 5,420 | 2,640 | 1,430 | 360 |
| petroleum | 3,010 | 1,970 | 490 | 195 |
| gasoline | 3,980 | 2,140 | 910 | 210 |

Example 5

A quantity of 1 kg of dry soil, contaminated with 20,000 mg of a mixture of crude-oil, contaminated oil and petroleum has been treated with 20 grams of BIOREM RC1. The following degradation rates have been achieved:

| Trial sample Mass of oil-derivates in milligrams per kg of dry soil (mg/kg) | | | |
|---|---|---|---|
| | Degradation period | | |
| | 10 days | 30 days | 40 days |
| crude oil | 13,200 (66.0%) | 7,120 (35.6%) | 890 (4.45%) |
| motor oil | 11,610 (58.05%) | 4,560 (22.8%) | 410 (2.05%) |
| petroleum | 9,980 (49.9%) | 3,120 (15.6%) | 310 (1.55%) |

The percentage of the actual remaining part of the oil-derivates in comparison to the initial value (100%) is indicated in parentheses.

Example 6

22m³ of oil-contaminated soil had been mixed with compost in a layer of 30 cm height outdoor. Every three days the soil has been loosened and turned. A first control of equally contaminated soil (No. 1) has only been mixed with compost, but not treated with BIOREM RC1. A second control (No. 2) has not been treated at all. The following results have been achieved:

| Trial sample Mass of oil-derivates in milligram per kg of dry soil (mg/kg) | | | | |
|---|---|---|---|---|
| | Degradation period | | | |
| | 0 days | 15 days | 35 days | 60 days |
| soil with compost and BIOREM RC1 | 1,698 (100.0%) | 267 (15.72%) | 151 (8.89%) | 98 (5.77%) |
| control No. 1 | 1,698 (100.0%) | 267 (69.26%) | 151 (53.71%) | 98 (38.7%) |
| control No. 2 | 1,698 (100.0%) | 1,656 (97.53%) | 1,589 (93.58%) | 1,504 (88.6%) |

The percentage of the actual remaining part of the oil-derivates in comparison to the initial value (100%) is indicated in parentheses.

Example 7

Biodegradation of oil-substances in mud, contaminated with heavy metals.

Concentration of oil-derivates in mud (mg per liter):

| Degradation period | | | |
|---|---|---|---|
| 3 days | 14 days | 21 days | 35 days |
| 78,600 ±170 | 91,500 ±130 | 29,400 ±140 | 9,300 ±90 |

Example 8

Biodegradation of oil-substances in waste water on a solid material (test period: 11th Jul. 1992 until 11th Oct. 1992):

| Concentration of oil-derivates in water (g per kg) | | | |
|---|---|---|---|
| Degradation period | | | |
| 0 days | 30 days | 60 days | 90 days |
| 84.39 | 64.50 | 38.22 | 8.64 |

Example 9

Biodegradation of motor oil in soil (on the occasion of an oil-spill accident).

| Method Concentration of oil-derivates in water (g per kg) | | | | | |
|---|---|---|---|---|---|
| | Degradation period: | | | | |
| | 0 days | 10 days | 20 days | 50 days | 90 days |
| Compost: | 813 | 564 | 380 | 309 | 217 |
| BIOREM RC1: | 813 | 407 | 317 | 185 | 119 |
| Compost and BIOREM RC1: | 813 | 413 | 254 | 137 | 91 |
| Control: | 813 | | | | 691 |

Example 10

Biodegradation of oil substances in a soil with an old contamination (test period: 13th Jul. 1992 until 19th Sep. 1992):

| Concentration of oil-derivates in mg/kg of soil | | | |
|---|---|---|---|
| Degradation period | | | |
| 0 days | 16 days | 36 days | 67 days |
| 1,626 | 280 | 164 | 128 |

Example 11

Biodegradation of transformer-oil in soil on the occasion of an oil-spill accident (test period: 31st Aug. 1992 until 26th Oct. 1992):

| Concentration of oil-derivates in mg/kg of soil | | | |
|---|---|---|---|
| Degradation period | | | |
| 0 days | 28 days | 45 days | 56 days |
| 16,180 | 5,434 | 2,562 | 781 |

As a comparative figure to these examples it may be mentioned that for the industrial degradation of a soil with 2,000 mg hydrocarbons per kg dry substance down to 282 mg per kg dry substance, approx. 30 weeks are regarded as a leading value (Journal TR Technische Rundschau, Das Schweizer Industriemagazin, Issue 3, 1993, page 28).

The artificially prepared mixture of microorganisms is stable in natural conditions. It is active in a wide range of the pH-value between 4.5 and 7.5 and in a temperature range of 5° C. to 35° C. A condition for the achievement of a maximal physiological activity is an optimal supply of oxygen (for the oxidation of 3.5 grams of crude mineral oil, 1 gram $O_2$ is needed in minimum) and the presence of a stiumulating substance. The mixture is capable of degrading the oil-hydrocarbons both in high contaminations (more than 10 g/l) as well as in relatively low contaminations (about 1 g/l). In both cases the concentration allowed by the respective norms may be detected after completion of the degradation.

The mixture of microorganisms is basically capable of disposing wastes which contain hydrocarbons, in particular mineral oil and its products, as well as to remove the results of ecological catastrophes in the course of which the soil or the water has been contaminated by mineral oil substances.

We claim:

1. A mixture of microorganisms for the biodegradation of hydrocarbons, comprising:

*Pseudomonas putida* and *Geotrichum candidum* in a cell-number ratio of 5:1 to 1:1.

2. The mixture of microorganisms according to claim 1, wherein the cell-number ratio of *Pseudomonas putida* to *Geotrichum candidum* is 1:1.

3. The mixture of microorganisms according to claim 1, wherein the cell-number ratio of *Pseudomonas putida* to *Geotrichum candidum* is 2:1.

4. The mixture of microorganisms according to claim 1, wherein the cell-number ratio of *Pseudomonas putida* to *Geotrichum candidum* is 3:1.

5. The mixture of microorganisms according to claim 1, wherein the cell-number ratio of *Pseudomonas putida* to *Geotrichum candidum* is 4:1.

6. The mixture of microorganisms according to claim 1, wherein the cell-number ratio of *Pseudomonas putida* to *Geotrichum candidum* is 5:1.

7. A mixture of microorganisms for the biodegradation of hydrocarbons, comprising:

*Pseudomonas putida* and *Geotrichum candidum* in a cell-number ratio of 5:1 to 1:1; and, a stimulation substance selected from the group consisting of nitrogen, phosphorous, at least one trace element and a combination thereof.

8. The mixture of microorganisms according to claim 7, wherein the cell-number ratio of *Pseudomonas putida* to *Geotrichum candidum* is 1:1.

9. The mixture of microorganisms according to claim 7, wherein the cell-number ratio of *Pseudomonas putida* to *Geotrichum candidum* is 2:1.

10. The mixture of microorganisms according to claim 7, wherein the cell-number ratio of *Pseudomonas putida* to *Geotrichum candidum* is 3:1.

11. The mixture of microorganisms according to claim 7, wherein the cell-number ratio of *Pseudomonas putida* to *Geotrichum candidum* is 4:1.

12. The mixture of microorganisms according to claim 7, wherein the cell-number ratio of *Pseudomonas putida* to *Geotrichum candidum* is 5:1.

13. A process for applying a mixture of microorganisms for a biodegradation of hydrocarbons, comprising the step of:

preparing a liquid preparation containing between 1–10 grams, per liter of water, of a mixture of microorganisms having *Pseudomonas putida* and *Geotrichum candidum* in a cell-number ratio of 5:1 to 1:1, said liquid preparation further including a stimulation substance selected from the group consisting of nitrogen, phosphorous, at least one trace element and a combination thereof; and, spraying 1–10 liters of said liquid preparation per square meter of soil contaminated by hydrocarbons.

14. The process for applying a mixture of microorganisms for a biodegradation of hydrocarbons according to claim 13, wherein said spraying step is carried out a plurality of times.

15. The process for applying a mixture of microorganisms for a biodegradation of hydrocarbons according to claim 13, further comprising the step of adding nitrogen to the soil following said spraying step, so that the ratio of carbon to nitrogen existing in the soil following said adding nitrogen step is 10:1 to 100:1.

16. The process for applying a mixture of microorganisms for a biodegradation of hydrocarbons according to claim 13, wherein said spraying step is carried out at a temperature between 5° C. to 35° C., and following said spraying step, the soil has a pH of between 4.5 to 7.5.

* * * * *